United States Patent [19]

Ghilardi et al.

[11] 4,020,162
[45] Apr. 26, 1977

[54] OXYTETRACYCLINE SOLUTION FOR PARENTERAL, PERORAL AND LOCAL ADMINISTRATION AND PROCESSES FOR THE PRODUCTION THEREOF

[75] Inventors: Hans Peter Ghilardi, Therwil; Kaya Atasoy, Munchenstein, both of Switzerland

[73] Assignee: Ciba-Geigy Corporation, Ardsley, N.Y.

[22] Filed: Feb. 7, 1975

[21] Appl. No.: 548,051

[30] Foreign Application Priority Data

Feb. 19, 1974  Switzerland ................ 2276/74

[52] U.S. Cl. .......................................... 424/227
[51] Int. Cl.$^2$ .................................... A61K 31/65
[58] Field of Search ............................ 424/227

[56] References Cited

UNITED STATES PATENTS

| | | | |
|---|---|---|---|
| 2,699,054 | 1/1955 | Conover | 424/227 |
| 3,017,323 | 1/1962 | Gordon et al. | 424/227 |

*Primary Examiner*—Albert T. Meyers
*Assistant Examiner*—Daren M. Stephens
*Attorney, Agent, or Firm*—Harry Falber

[57] ABSTRACT

The present invention relates to an aqueous oxytetracycline solution for parenteral, peroral and local administration, which contains, in addition to the active substance present as base or as salt, polyethylene glycol having a mean molecular weight of 300 to 600, a soluble magnesium salt, a base, preservatives and a buffer system, and to a process for producing this solution.

7 Claims, No Drawings

OXYTETRACYCLINE SOLUTION FOR PARENTERAL, PERORAL AND LOCAL ADMINISTRATION AND PROCESSES FOR THE PRODUCTION THEREOF

The present invention relates to an aqueous oxytetracycline solution for parenteral, peroral and local administration, which contains, in addition to the active substance present as base or as salt, polyethylene glycol, a soluble magnesium salt, a base, preservatives and a buffer system, and to a process for producing this solution.

An essential prerequisite for the practical applicability of oxytetracycline solutions is their chemical and physical stability with regard to storage and transport with retainment of good compatibility.

To attain this end, several attempts known from the literature have been made, and proposals for solving this problem have been put forward. In the English Patent Specification No. 894,619 there is recommended, besides the use of magnesium salts as complex-formers for oxytetracycline, inter alia, polyethylene glycol 300 as solubility-promoting agent with a water content of up to 30 percent by weight for the preparation of oxytetracycline solutions. The U.S. Pat. No. 3,017,323 describes the formation of metal-ion complexes of oxytetracycline in polyethylene glycol 400 with concentrations of up to 70 percent by weight, but likewise with the limitation of the water content to 0 to 25 percent by weight, the reason given being that higher proportions of water clearly impair the stability of oxytetracycline solutions. A further suggestion is made in the German Offenlegungsschrift No. 2,001,604, according to which there are to be used for the preparations, in addition to the active substance, inter alia, polyethylene glycols having molecular weights of 1000 to 20,000 with a water content of 60 to 80 percent by weight.

The oxytetracycline solutions containing polyethylene glycols and water hitherto known from the literature vary considerably with respect to the stated ingredients. There are suggested on the one hand solutions with low concentrations of polyethylene glycol of higher molecular weight in addition to a high proportion of water, on the other hand solutions with higher concentrations of polyethylene glycol but low molecular weight and with a low proportion of water. These differing concentration conditions are closely connected with the known secondary effects of solubility-promoting polyethylene glycols. Thus, the polyethylene glycols of higher molecular weight are desirable, for reasons of toxicity, only in lower concentration. The inevitably resulting high proportion of water caused in the case of prior formulations in general a considerable lowering of the stability of the solutions. The polyethylene glycols of lower molecular weight, known to be less toxic, have however hitherto been used in higher concentrations because the aim was to thus obtain an adequate solubility of the active substance as well as an improvement in the stability of the solution; this on the other hand resulted, on account of the occurrence of high osmotic pressure, in an unfavourable influencing of the compatibility, particularly in the case of parenteral administration. Reference is expressly made to these causalities both in the U.S.A. Patent Specification No. 3,017,323 and in the German Offenlegungsschrift No. 2,001,604. The oxytetracycline solutions suggested in the stated German Offenlegungsschrift do contain — as already mentioned — high water contents of 60 - 80 percent by weight; they render possible however the use only of polyethylene glycols of which the molecular weight must not fall below 1000. A further disadvantage of the oxytetracycline formulations that have hitherto become known arises from the fact that their storage stability, expecially in the non-cooled condition, leaves much to be desired.

It has been possible with the oxytetracycline solutions according to the invention to overcome, in a surprising manner, both the prejudice of the experts to the formulation of oxytetracycline solutions with polyethylene glycols of low molecular weight of essentially below 1000 with, at the same time, a high content of water and the disadvantages, particularly with regard to stability, connected with the known preparations. Thus, in producing the oxytetracycline solutions according to the invention, there are used, in addition to a water content of up to 80 percent by weight, as solubility-promoting agents, non-toxic polyethylene glycols having a molecular weight of 300 to 600. The solutions contain in detail oxytetracycline in the form of the free base or as salt, a soluble magnesium salt, polyethylene glycol, preservatives, a base and a buffer system, with a water content of 40 to 80 percent by weight. They are characterized in that the polyethylene glycol has a mean molecular weight of 300 to 600, preferably 400.

The process of the invention for the production of oxytetracycline solutions is characterised in that oxytetracycline is suspended in the form of the free base or as salt in polyethylene glycol having a mean molecular weight of 300 to 600, preferably 400, and there are then added, with the passing through of nitrogen, aqueous magnesium salt solution, a base, a preservative, and a buffer solution consisting of tris-(hydroxymethyl)-aminomethane hydrochloride and water.

With the use of oxytetracycline in the salt form, the hydrochloride is employed.

By magnesium salt is meant magnesium chloride.

Molar ratios of 1:1 to 1:4 for oxytetracycline to magnesium salt have a favourable effect on the properties of the solutions.

The polyethylene glycols used are commercial types of pharmaceutical purity (according to DAB or PH VI, or of an analogous quality). The polyethylene glycol having a molecular weight of 400 has proved particularly safe from a toxicological point of view.

Suitable as a base are NaOH and ethanolamine, while sodium formaldehyde sulphoxylate or sodium meta-bisulphite can be used as a preservative. Also suitable is ascorbic acid alone or in combination with sodium meta-bisulphite.

Tris-(hydroxymethyl)-aminomethane-hydrochloride is used as a buffer system, as a result of which a favourable effect on the stability of the solutions is achieved.

The oxytetracycline solutions of the invention are chemically and physically very stable, so that even at room temperature they are storable over a prolonged period of time. No impairment of compatibility on parenteral administration was detected. The oxytetracycline solutions according to the invention moreover render possible, without disadvantages, the formulation of active-substance concentrations of 1 to 12 percent by weight. As far as the higher concentrations are concerned there accrue, particularly in the case of veterinary medicine, substantial advantages. It is thus possible, since the administered dose is usually related to the body weight of the animal to be treated, to lower the frequency of administration, which leads to a reduction of the medication stress.

Regarding formulations constituting for the invention a particularly favourable embodiment, the concentration of the individual constituents is in the following ranges:

oxytetracycline or oxytetracycline-HCl: 4 – 11%;
polyethylene glycol: 18 – 28%;
$MgCl_2$: : 2.5 – 5.5%;
ethanolamine: 1.3 – 4.3%;
preservative: 0.4 – 0.5%;
tris-(hydroxymethyl)-aminomethane: 0.10 – 0.35%;
0.1N HCl: 2.0 – 8.5%;
$H_2O$ (total): 48 – 75%.

The invention is illustrated by the following examples:

EXAMPLE 1

5.4 g of oxytetracycline hydrochloride is suspended in 20.0 g of polyethylene glycol 400. There are subsequently added, with stirring and passing through of $N_2$, 30.6 g of 10% magnesium chloride solution, 23,75 g of 10% ethanolamine solution, 0.5 g of sodium formaldehyde sulphoxylate and 27.67 g of buffer solution consisting of 0.167 g of trishydroxymethylaminomethane, 4.192 g of 0.1N HCl and 23.311 g of water. The pH of this solution is 8.6 and the water content 72.23%. The solution has an active-substance content of 54 mg of oxytetracycline HCl/ml.

EXAMPLE 2

5.4 g of oxytetracycline hydrochloride is suspended in 25 g of polyethylene glycol 400. There are then added, with stirring and passing through of $N_2$, 30.6 g of 10% magnesium chloride solution, 22.4 g of 10% ethanolamine solution, 0.5 g of sodium formaldehyde sulphoxylate and 23.0 g of buffer solution consisting of 0.139 g of trishydroxymethylaminomethane, 3.48 g of 0.1N HCl and 19.381 g of water. The pH of this solution is 8.5 and the water content 67%. The solution has an active-substance content of 54 mg of oxytetracycline HCl/ml.

EXAMPLE 3

0.351 g of trishydroxymethylaminomethane is dissolved in 48.862 g of water, whereupon 8.787 g of 0.1N HCl is added. In 50 g of this buffer solution there is then added 5.5 g of magnesium chloride. In the remaining 8.0 g of buffer solution, there is separately dissolved 0.5 g of sodium formaldehyde sulphoxylate. These solutions are subsequently added successively, with the passing through of $N_2$, to a suspension of 10.8 g of oxytetracycline, 30.0 g of polyethylene glycol 400 and 4.48 g of ethanolamine. There is obtained a clear yellow solution having a pH-value of 8.5 and a water content of 48.8%. The active-substance content is 10.8 mg of oxytetracycline/ml.

EXAMPLE 4

6.21 g of oxytetracycline HCl is suspended in 20.0 g of polyethylene glycol 400, whereupon there are added, with stirring and passing through of nitrogen, 35.20 g of 10% magnesium chloride solution, 25.5 g of 10% ethanolamine solution, 0.5 g of sodium formaldehyde sulphoxylate and 19.23 g of tris-buffer solution. The last-mentioned consists of 0.12 g of trishydroxymethylaminomethane, 2.49 g of HCl (0.1N) and 16.62 g of water. There is formed a light-yellow solution having a pH-value of 8.6, a water content of 71.3% and an active-substance content of 62.1 mg/ml.

EXAMPLE 5

5.50 g of oxytetracycline base is suspended in 20.0 g of polyethylene glycol 400. There are then added to this suspension, with stirring and passing through of nitrogen, 35.2 g of 10% magnesium chloride solution, 15.8 g of 10% ethanolamine solution and 0.5 g of sodium formaldehyde sulphoxylate. The solution is made up to 100 ml with 29.35 g of tris-buffer solution containing 0.18 g of trishydroxymethylaminomethane, 3.81 g of 0.1N HCl and 25.36 g of water. The clear light-yellow solution has a pH-value of 8.6, a water content of 71.2% and an active-substance content of 55.0 mg/ml of oxytetracycline base.

EXAMPLE 6

5.75 g of oxytetracycline base is suspended in 20.0 g of polyethylene glycol 400. There are then added to this suspension, with passing through of nitrogen and with stirring, 35.2 g of 10% magnesium chloride solution, 16.6 g of 10% ethanolamine solution, 0.5 g of sodium formaldehyde sulphoxylate and 28.91 g of tris-buffer solution consisting of 0.18 g of trishydroxymethylaminomethane, 3.76 g of 0.1N HCl and 24.97 g of water. The clear light-yellow solution has a pH-value of 8.6, a water content of 71.59% and an active-substance content of 57.5 mg/ml of oxytetracycline base.

EXAMPLE 7

To 9.45 g of a 33.3% solution of ethanolamine there are added 11.0 g of a 50% solution of magnesium chloride, 0.5 g of sodium formaldehyde sulphoxylate and 30.0 g of polyethylene glycol 400. In this solution there is then dissolved, with passing through of nitrogen and with stirring, 11.0 g of oxytetracycline base. The solution is subsequently made up to 100 ml with 47.97 g of tris-buffer solution. The tris-buffer solution consists of 0.29 g of trishydroxymethylaminomethane, 6.24 g of 0.1N hydrochloric acid and 41.44 g of water. The clear light-yellow solution has a pH-value of 8.5, a water content of 53.2% and an active-substance content of 110 mg of oxytetracycline base/ml.

The water to be used in the Examples should be pyrogen-free.

We claim:

1. A process for the production of oxytetracycline solutions which comprises suspending 4–11% oxytetracycline in the form of the free base or the hydrochloride salt in 18–28% polyethylene glycol having a mean molecular weight of about 300 to 600, and thereafter admixing therewith in the presence of a nitrogen gas stream, 2.5–5.5% magnesium chloride, 1.3–4.3% of a base, 0.4–0.5% of a preservative, tris-(hydroxymethyl)-aminomethane-hydrochloride in a total concentration of 0.1–0.35% amino methane and 2.0–8.5% 0.1N HCl and 40–80%, by weight, of water; said concentration being based on the weight of the total solution.

2. An aqueous oxytetracycline solution for parenteral, peroral and local administration, which comprises, 4–11% of oxytetracycline in the form of the free base or the hydrochloride salt, 2.5–5.5% of magnesium chloride, 18–28% of polyethylene glycol having a mean molecular weight of about 300 to 600, 1.3–4.3% of a base, 0.4–0.5% of a preservative for said solution, tris-(hydroxymethyl)-aminomethane-hydrochloride in a total concentration of 0.1–0.35% aminomethane and 2.0%–8.5% 0.1N HCl, and 40 to 80% of water; said concentrations being based on the weight of the total solution.

3. Oxytetracycline solution according to claim 2, characterised in that the polyethylene glycol has a mean molecular weight of 400.

4. Oxytetracycline solution according to claim 2, characterised in that the pH-value of the solution is between 8.0 and 9.0.

5. Oxytetracycline solution according to claim 4, characterised in that the pH-value of the solution is between 8.5 and 8.9.

6. Oxytetracycline solution according to claim 2, characterised in that the molecular ratio of oxytetracycline to magnesium chloride is 1:1 to 1:4.

7. Process according to claim 1, characterised in that the polyethylene glycol has a mean molecular weight of 400.

* * * * *